United States Patent [19]

Farnos et al.

[11] Patent Number: 5,614,079
[45] Date of Patent: *Mar. 25, 1997

[54] CATALYTIC DEWAXING OVER SILICA BOUND MOLECULAR SIEVE

[75] Inventors: Maria D. Farnos, Wilmington, Del.; Thomas R. Forbus, Jr., Newtown, Pa.; John P. McWilliams, Woodbury; David S. Shihabi, Pennington, both of N.J.

[73] Assignee: Mobil Oil Corporation, Fairfax, Va.

[ * ] Notice: The term of this patent shall not extend beyond the expiration date of Pat. No. 5,365,003.

[21] Appl. No.: 315,291

[22] Filed: Sep. 29, 1994

Related U.S. Application Data

[63] Continuation-in-part of Ser. No. 22,220, Feb. 25, 1993, Pat. No. 5,365,003.

[51] Int. Cl.$^6$ .......................... C10G 25/00; C10G 47/02; C07C 4/02; B01J 29/06
[52] U.S. Cl. .......................... 208/27; 208/111; 585/752; 502/68; 502/73; 502/77
[58] Field of Search .................. 208/27, 111; 502/68, 502/77, 73; 585/752

[56] References Cited

U.S. PATENT DOCUMENTS

| | | |
|---|---|---|
| Re. 28,398 | 4/1975 | Chen et al. . |
| 3,684,695 | 8/1972 | Neel et al. . |
| 3,700,585 | 10/1972 | Chen et al. . |
| 3,755,145 | 8/1973 | Orkin . |
| 3,894,938 | 7/1975 | Gorring et al. . |
| 3,956,102 | 5/1976 | Chen et al. . |
| 3,968,024 | 7/1976 | Gorring et al. . |
| 3,969,274 | 7/1976 | Frampton . |
| 4,137,148 | 1/1979 | Gillespie et al. . |
| 4,176,050 | 11/1979 | Chen et al. . |
| 4,181,598 | 1/1980 | Gillespie et al. . |
| 4,222,855 | 9/1990 | Pelrine et al. . |
| 4,229,282 | 10/1980 | Peters et al. . |
| 4,247,388 | 1/1981 | Banta et al. . |
| 4,259,170 | 5/1981 | Graham et al. . |
| 4,259,174 | 5/1981 | Chen et al. . |
| 4,283,271 | 8/1981 | Garwood et al. . |
| 4,283,272 | 8/1981 | Garwood et al. . |
| 4,347,121 | 8/1982 | Mayer et al. . |
| 4,372,839 | 2/1983 | Oleck et al. . |
| 4,383,913 | 5/1983 | Powell et al. . |
| 4,414,097 | 11/1983 | Chester et al. . |
| 4,437,975 | 5/1984 | Gillespie et al. . |
| 4,524,232 | 6/1985 | Chester et al. . |
| 4,582,815 | 4/1986 | Bowes . |
| 4,597,854 | 7/1986 | Penick . |
| 4,605,488 | 8/1986 | Chester et al. . |
| 4,631,267 | 12/1986 | Lachman et al. . |
| 4,637,995 | 1/1987 | DeAngelis et al. . |
| 4,657,880 | 4/1987 | Lachman et al. . |
| 4,784,747 | 11/1988 | Shihabi ........................... 208/11 |
| 4,808,296 | 2/1989 | Chen et al. ..................... 208/11 |
| 5,053,374 | 10/1991 | Absil et al. . |
| 5,182,242 | 1/1993 | Marler . |
| 5,246,568 | 9/1993 | Forbus et al. . |
| 5,316,993 | 5/1994 | Sextl et al. ...................... 502/68 |
| 5,365,003 | 11/1994 | Chang et al. ................... 585/470 |

OTHER PUBLICATIONS

Chen and Garwood—"Industrial Application of Shape Selective Catalysis", Catal. Rev.–Sci: Eng. (1986) 28 (2 & 3): pp. 241–247.

Lachmam and Williams—"Extruded Monolithic Catalyst Supports", Symposium on Catalyst Supports: Chemistry, Forming and Characteristics, American Chemical Society, New York City Meeting (1991) pp. 535–543.

Kirk–Othmer Concise Encyclopedia of Chemical Technology, John Wiley & Sons, Inc., New York 1985, pp. 1062–1065.

Primary Examiner—Glenn A. Caldarola
Assistant Examiner—In Suk Bullock
Attorney, Agent, or Firm—P. W. Roberts

[57] ABSTRACT

A molecular sieve catalyst is composited with an inert binder derived from an organic silicon source and organic polymer. The catalyst is used in dewaxing of petroleum chargestocks.

6 Claims, No Drawings

1

CATALYTIC DEWAXING OVER SILICA BOUND MOLECULAR SIEVE

CROSS-REFERENCE TO RELATED APPLICATION

This application is a continuation-in-part of U.S. patent application Ser. No. 08/022,220, now U.S. Pat. No. 5,365,003 filed Feb. 25, 1993.

BACKGROUND OF THE INVENTION

1. Field of the Invention

The present invention is directed to catalytic dewaxing of petroleum chargestocks over a molecular sieve catalyst composition having an inert binder of large pore size, the preparation of the catalyst composition, and the catalyst composition.

2. Description of the Prior Art

Lube base stock oils are derived from various crude oil stocks by a variety of refining processes directed toward obtaining a lubricant base stock of suitable boiling point, viscosity index (VI), cloudpoint, overnight clouding and other characteristics. Generally, the base stock will be produced from the crude oil by distillation of the crude in atmospheric and vacuum distillation towers. The distillation provides one or more raw stocks within the boiling range of about 450° F. to 1010° F. (232°∝566° C.). The raw stocks are subjected to the separation of undesirable aromatic components and finally, to dewaxing and various finishing steps. Because aromatic components lead to high viscosity and extremely poor viscosity indices, the use of asphaltic type crudes is not preferred as they contain large quantities of aromatic components and yield extremely low levels of acceptable lube stocks. Paraffinic and naphthenic crude stocks are preferred but aromatic separation procedures will still be necessary to remove aromatics. In the case of lubricant distillate fractions, generally referred to as the neutrals, e.g., heavy neutral, light neutral, etc. the aromatics will be extracted by solvent extraction using a solvent such as furfural, n-methyl-2-pyrrolidone, phenol or other material which is selective for the extraction of the aromatic components. The residue recovered from such a solvent extraction of aromatics is called a raffinate. The raffinate is relatively free of aromatics and therefore has improved viscosity indices, but still contains paraffins which adversely effect the pour point and other properties. With the heavier residuum from the lower portion of the vacuum tower (short residuum), asphaltenes will first be removed in a deasphalting step, e.g., with propane, followed by solvent extraction of residual aromatics to produce a heavy raffinate generally referred to as bright stock. In either case, with lighter raffinates or bright stock, a further catalytic dewaxing step is normally necessary to reduce waxy paraffins in order for the lubricant to have a satisfactorily low pour point and cloud point, so that the lubricant will not solidify or precipitate under low temperature conditions. The term dewaxing means the removal of those hydrocarbons (waxes) which will readily solidify.

Dewaxing has been carried out both catalytically and with solvents. In solvent dewaxing, a solvent such as a mixture of methyl ethyl ketone (MEK) and toluene or liquid propane is used, followed by chilling to induce crystallization of the paraffin waxes for removal.

Catalytic dewaxing processes are described, for example, in U.S. Pat. Nos. 3,700,585, Re. 28,398, 3,956,102 and 3,968,024. A subsequent hydrotreating step may be used to stabilize the product by saturating lube boiling range olefins produced by the selective cracking which takes place during catalytic dewaxing. Reference is made to U.S. Pat. Nos. 4,181,598 and 4,437,975 for descriptions of such processes.

A dewaxing process employing synthetic offretite is described in U.S. Pat. No. 4,259,174. Processes of this type have become commercially available as shown by the 1986 Refining Process Handbook, page 90, Hydrocarbon Processing, September 1986, which refers to the availability of the Mobil Lube Dewaxing Process (MLDW). The MLDW process is also described in Chen et al., "Industrial Application of Shape-Selective Catalysis" Catal. Rev. Sci. Eng. 28, (283), 185–264 (1986), especially pp. 241–247, to which reference is made for a further description of the process. Reference is made to these disclosures for a description of various catalytic dewaxing processes. Catalytic dewaxing processes generally utilize ZSM-5 type catalysts.

Generally, light raffinates dewaxed with ZSM-5 catalysts suffer some losses in yield and viscosity indices relative to solvent dewaxing to identical pour points. Zeolites with more constrained pores and therefore greater selectivity such as zeolites from the ferrierite family, i.e., ZSM-22, 23, 35, 57 and 58, have been used to recapture some of these losses. Processes of this type are described, for example, in U.S. Pat. Nos. 4,222,855, 4,372,839, 4,414,097, 4,524,232 and 4,605,888. Although some of these more constrained catalysts perform relatively well with light hydroprocessed feeds, they typically have difficulty in or are incapable of processing non-hydroprocessed and even heavier hydroprocessed feeds.

In addition, in the dewaxing of heavy raffinates such as bright stock, the presence of large waxy naphthenic-type molecules (cycloparaffins) cause hazing which results from the formation of microcrystalline wax particles that can occur over time at low storage temperatures in the range of the pour point of the stock. Haze prevention in lubricant basestocks and products is desired for appearance as well as the engineering function of insuring good low temperature pumpability and filterability in certain lubrication systems, especially in systems where fine filtration is required for maintaining critical lubricant cleanliness. The naphthenic-type molecules involved in haze formation occur naturally in petroleum.

Dewaxing of lubricant basestocks removes much of these troublesome components, especially solvent dewaxing, e.g., with methyl ethyl ketone (MEK) and toluene. In catalytic dewaxing of heavy raffinates, however, these components are not easily removed and they can be left behind in the basestock. For this reason, catalytically dewaxed bright stock raffinate basestocks suffer poorer low temperature hazing characteristics relative to basestocks processed to similar pour point through solvent dewaxing. In order to mitigate this problem, catalytic conversion to lower point is practiced. This, however, results in lower basestock yields and shorter process cycles (faster catalyst aging) in catalytic dewaxing. With some particularly troublesome feedstocks, this problem cannot always be easily or economically remedied with current catalytic dewaxing technology.

Zeolite catalysts have often been incorporated with a matrix or binder material to impart strength during hydrocarbon conversion processes. The most commonly used matrix materials include alumina, clay and amorphous silica derived from inorganic sources. Binder materials may contribute chemical properties such as acidity and physical properties such as surface area and high or low density. The aluminas may have activity; for example, gamma alumina has Lewis acid sites and Bronsted acidity. Amorphous silica, on the other hand, has low activity. Silica gel is three-dimensional network of particles of colloidal silica and may be of regular, intermediate or low density. The hydrous clays are generally chemically inactive but some are chemically modified for activity.

The use of a steamed porous silica gel as a support is described in U.S. Pat. No. 3,369,274. U.S. Pat. No. 4,582,815 describes a catalyst produced by mulling silica, a zeolite, water and a base such as sodium hydroxide. U.S. Pat. No. 5,182,242 describes extruding zeolite, low activity refractory oxide binder such as silica wherein the silica is derived from an inorganic silica rich solid such as amorphorous silica or hydrated silica in which the silica concentration is at least 50%.

None of the binder materials previously described encompasses an inert binder of large pore size nor an organic silicon source for the binder.

SUMMARY OF THE INVENTION

The invention is a process for catalytically dewaxing a hydrocarbon feedstock by contacting with a catalyst composition which includes a zeolite in an inert binder.

The catalyst composition is prepared by mulling zeolite crystals, organosilicon compound, organic polymer and an extrusion facilitating amount of liquid to form an extrusion mixture, extruding the mixture and calcining the extrudate.

Advantageously, substantial basestock yield and viscosity indices (V.I.) improvements are seen when utilizing the catalyst composition in dewaxing of light neutral as well as heavy raffinates. In a further advantage, conversion conditions of reduced severity may be used without compromising yield or V.I. These less severe conditions allow longer cycle lengths.

DETAILED DESCRIPTION OF THE INVENTION

Zeolite crystals to be used in commercial processes are generally formed into agglomerates for improved strength and resistance to attrition. To form the catalyst composition herein, the zeolite crystals are composited with binder precursor materials by agglomeration. Various methods may be used for agglomeration. These methods include extrusion into pellets or beads, spray-drying into fluidizable microspheres, or hot pressing into tablets. Extrusion is the preferred mode of agglomeration. The pellet size of the extrudate is preferably from about 1/32 inch to about 1/8 inch. For dewaxing, the zeolite preferably has a Constraint Index of 1 to 12 and more preferably has the structure of ZSM-5.

The binder precursor materials include organosilicon compound and an organic polymer.

The organosilicon compounds include silanes such as alkylsilanes, arylsilanes, alkylarylsilanes, alkoxysilanes, aryloxysilanes, oxethylenesilanes, alkyaryloxysilanes, siloxanes and polysiloxanes with alkyl and/or aryl and/or glycol groups. Alkyl preferably includes 1 to 12 carbons. Alkyl preferably includes 6 to 10 carbons.

The preferred organosilicon compounds are silicones, particularly quadrifunctional silicones having relatively few organic groups and silicone resins which are solid at room temperature. Particularly preferred are silicones such as Q6-2230 silicone resin manufactured by Dow Corning.

Silicones are polysiloxanes containing a repeating silicon-oxygen backbone and organic groups attached to a proportion of the silicon atoms by silicon-carbon bonds.

The molecular structure of silicones can include linear, branched and/or cross-linked structures. Silane monomers are the precursors of silicones and the nomenclature of silicones makes use of the letters M, D, T and Q to represent monofunctional difunctional, trifunctional and quadrifunctional monomer units. Primes, e.g., D' are used to indicate substituents other than methyl. Examples of formulas and their corresponding symbols for silicones are as follows:

| Formula | Functionality | Symbol |
| --- | --- | --- |
| $(CH_3)_3SiO_{0.5}$ | mono | m |
| $(CH_3)_2SiO$ | di | D |
| $(CH_3)SiO_{1.5}$ | tri | T |
| $(CH_3)(C_6H_5)SiO$ | di | D' |
| $(CH_3)(H)SiO$ | di | D' |
| $SiO_2$ | quadri | Q |

Silicones may be cross-linked to form silicone resins.

For further discussion of silicones see Kirk-Othmer Concise Encyclopedia of Chemical Technology, John Wiley & Sons, Inc., New York 1985, pages 1062–1065.

Silicone compounds which can be used as binder precursor materials in the present invention can be characterized by the general formula:

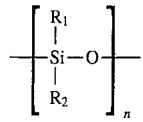

where R is hydrogen, halogen, hydroxy, alkyl, aryl, alkylaryl or fluoro-alkyl. The hydrocarbon substituents for $R_1$ and $R_2$ generally independently contain from 1 to 10 carbon atoms and preferably are methyl or ethyl groups, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, polydimethylsilicone, methylvinylsilicone, ethylvinylsilicone and silicone.

The organosilicon compound may be dry blended with the zeolite crystals. Alternatively, the organosilicon compound may be added in the form of an emulsion or solution. The zeolite crystals and organosilicon compound are added to the extrusion mixture in an amount such that, after extrusion and calcination, the extrudate contains from 50 to 95 parts by weight (wt. %) zeolite and from 5 to 50 parts by weight (wt. %) silica.

Additional polymeric organic material is added to the extrusion mixture. The additional organic materials include as non-limiting examples, polyacrylonitrile, cellulose or derivatives thereof, phenol/formaldehyde resins, polyfurfuryl alcohol, polyimides, polyesters, polyolefins, acrylic resins, polyvinylalcohol, styrene resins or polycarbonate. Preferred are cellulose or derivatives thereof, polyacrylonitrile, phenol/formaldehyde resins, polyfurfuryl alcohol and polyimides. More preferred is hydrated methyl cellulose. The organic material is added in an amount of about 0.1 to 5 wt. % of the extrudate mixture.

The extrusion mixture also includes an organic or inorganic dispersant or solvent such as water, alcohols, e.g., isopropanol; polar organic esters; ethers or mixtures thereof in an amount sufficient to facilitate mulling. The preferred dispersants or solvents are water alcohols and/or polar organic esters. While organic alcohols are useful, their volatility may require vapor recovery in the mulling and extrusion steps.

Following extrusion, the extrudate is calcined. For example, the catalyst may be calcined in an oxygen-containing atmosphere, preferably air, at a rate of 0.2° to 5° C./minute to a temperature greater 300° C. but below a temperature at which the crystallinity of the zeolite is adversely affected. Generally, such temperature will be below 600° C. Preferably the temperature of calcination is within the approximate range of 350° to 550° C. The product is maintained at the calcination temperature usually for 1 to 24 hours.

While it is not intended to be bound by any one theory, it is theorized that the organic material in the extrusion mixture burns off during calcination leaving behind void spaces (large pores) within the microstructure of the binder material.

After calcination, the catalyst composition has a majority of its pore volume, e.g., preferably above 60% of pore volume, more preferably above 75% of pore volume, in the large size range, e.g., of a size of about 300 Angstroms or greater.

The binder material is also characterized as being inert. By inert is meant having low activity, in contrast to, for example, gamma alumina which has Lewis acid sites and Bronsted acidity.

The calcined extrudate may be steamed in an atmosphere of 0% to 100% water vapor at a temperature of 200° C. to 500° C. and a pressure of 0.1 to 1 atm for 1 to 48 hours.

In the dewaxing process of the invention, a lube feedstock, typically a 650° F. + (345° C. +) feedstock, is subjected to dewaxing over the catalyst composition. For dewaxing, the preferred zeolite is a ZSM-5 aluminosilicate, preferably in the hydrogen form. The hydrogen or decationized or "acid" form of the zeolite is readily formed in the conventional way by cation exchange with an ammonium salt followed by calcination to decompose the ammonium cations, typically at temperatures above about 800° F. (about 425° C.), usually about 1000° F. (about 540° C.). Dewaxing catalysts containing the acid form zeolite are conveniently produced by compositing the zeolite with the binder and forming the catalyst particles followed by ammonium exchange and calcination. If the zeolite has been produced using an organic directing agent, calcination prior to the cation exchange step is necessary to remove the organic from the pore structure of the zeolite; this calcination may be carried out either in the zeolite itself or the matrixed zeolite. The zeolite catalyst composition may contain a hydrogenation/dehydrogenation component such as nickel or may be free of any such component as described in European Patent Publication 426,841.

Feedstock

The hydrocarbon feedstock is a lube range feed with an initial boiling point and final boiling point selected to produce a lube stock of suitable lubricating characteristics. The feed is conventionally produced by the vacuum distillation of a fraction from a crude source of suitable type. Generally, the crude will be subjected to an atmospheric distillation and the atmospheric residuum (long resid) will be subjected to vacuum distillation to produce initial lube stocks (raw stocks). The vacuum distillate stocks or neutral stocks used to produce relatively low viscosity paraffinic products which typically range from 50 SUS (10 centistockes or cSt) at 40° C. for a light neutral to about 1000 SUS (215 cSt) at 40° C. for a heavy neutral. The distillate fractions are usually subjected to solvent extraction of aromatics to improve their V.I. and other qualities using a solvent which is selective for aromatics such as furfural, phenol or N-methyl-pyrrolidone. The vacuum resid (short resid) may be used as a source of more viscous lubes after deasphalting, usually by propane deasphalting (PDA) followed by solvent extraction to remove undesirable, high viscosity, low V.I. aromatic components. This raffinate is generally referred to as Bright Stock and typically has a viscosity of 100 to 300 SUS at 100° C. (21 to 61 cSt).

Lube range feeds may also be obtained by other procedures whose general objective is to produce an oil of suitable lubricating character from other sources, including marginal quality crudes, shale oil, tar sands and/or synthetic stocks from process such as methanol or olefin conversion or Fischer-Tropsch synthesis. The lube hydrocracking process is especially adapted to use in a refinery for producing lubricants from asphaltic or other marginal crude sources because it employs conventional refinery equipment to convert the relatively aromatic (asphaltic) crude to a relatively paraffinic lube range product by hydrocracking. Integrated all-catalytic lubricant producing processes employing hydrocracking and catalytic dewaxing are described in U.S. Pat. Nos. 4,414,097, 4,283,271, 4,283,272, 4,383,913, 4,347,121, 3,684,695 and 3,755,145. Processes for converting low molecular weight hydrocarbons and other starting materials to lubestocks are described, for example, in U.S. Pat. Nos. 4,547,612, 4,547,613, 4,547,609, 4,517,399 and 4,520,221, to which reference is made for a description of these processes.

The lube stocks used for making turbine oil products are the neutral or distillate stocks produced from selected crude sources during the vacuum distillation of a crude source, preferably of a paraffinic nature such as Arab Light crude. Turbine oils are required to possess exceptional oxidative and thermal stability and generally this implies a relatively paraffinic character with substantial freedom from excessive quantities of undesirable aromatic compounds, although some aromatic content is desirable for ensuring adequate solubility of lube additives such as anti-oxidants, and anti-wear agents. The paraffinic nature of these turbine oil stocks will, however, often imply a high pour point which needs to be reduced by removing the waxier paraffins, principally the straight chain n-paraffins, the monomethyl paraffins and the other paraffins with relatively little chain branching.

General Process Considerations

Prior to catalytic dewaxing, the feed may be subjected to conventional processing steps such as solvent extraction, if necessary, to remove aromatics or to hydrotreating under conventional conditions to remove heteroatoms and possibly to effect some aromatics saturation or to solvent dewaxing to effect an initial removal of waxy components.

In general terms, these catalytic dewaxing processes are operated under conditions of elevated temperature, usually ranging from about 400° F. to 900° F. (about 205° C. to 485° C.), but more commonly from about 500° F. to 850° F. (about 260° C. to 450° C.), depending on the dewaxing severity necessary to achieve the target pour point for the product.

As the target pour point for the product decreases the severity of the dewaxing process will be increased so as to effect an increasingly greater removal of paraffins with increasingly greater degrees of chain branching, so that lube yield will generally decrease with decreasing product pour point as successively greater amounts of the feed are converted by the selective cracking of the catalytic dewaxing to higher products boiling outside the lube boiling range. The V.I. of the product will also decrease at lower pour points as the high V.I. iso-paraffins or relatively low degree of chain branching are progressively removed.

In addition, the temperature is increased during each dewaxing cycle to compensate for decreasing catalyst activity, as described above. The dewaxing cycle will normally be terminated when a temperature of about 700° F. (about 370° C.) is reached since product stability can be harmed at higher temperatures.

Hydrogen is not required stoichiometrically but promotes extended catalyst life by a reduction in the rate of coke laydown on the catalyst. ("Coke" is highly carbonaceous hydrocarbon which tends to accumulate on the catalyst during the dewaxing process.) The process is therefore carried out in the presence of hydrogen, typically at 200–800 psig (about 1385 to 5536 kPa, abs.) although higher pressures can be employed. Hydrogen circulation rate is typically 1000 to 4000 SCF/bbl, usually 2000 to 3000 SCF/bbl of liquid feed (about 180 to 710, usually about 355 to 535 to 535 $n.1.1.^{-1}$). Space velocity will vary according to the chargestock and the severity needed to achieve the target pour point but is typically in the range of 0.25 to 5 LHSV ($hr^{-1}$), usually 0.5 to 2 LHSV.

In order to improve the quality of the dewaxed lube products, a hydrotreating step follows the catalytic dewaxing in order to saturate lube range olefins as well as to remove heteroatoms, color bodies and, if the hydrotreating pressure is high enough, to effect saturation of residual aromatics. The post-dewaxing hydrotreating is usually carried out in cascade with the dewaxing step so that the relatively low hydrogen pressure of the dewaxing step will prevail during the hydrotreating and this will generally preclude a significant degree of aromatics saturation. Generally, a hydrotreating will be carried out at temperatures from about 400° F. to 600° F. (about 205° to 315° C.), usually with higher temperature for residual fractions (bright stock), for example, about 500° to 575° F. (about 260° to 300° C.) for bright stock and, for example, about 425° to 500° F. (about 220° to 260° C.) for the neutral stocks. System pressures will correspond to overall pressures typically from 400 to 1000 psig (2860 to 7000 kPa, abs.) although lower and higher values may be employed e.g. 2000 or 3000 psig (about 13890 kPa or 20785 abs.). Space velocity in the hydrotreater is typically from 0.1 to 5 LHSV ($hr^{-1}$), and in most cases from 0.5 to 2 $hr^{-1}$.

Processes employing sequential lube catalytic dewaxing-hydrotreating are described in U.S. Pat. Nos. 4,181,598 4,137,148 and 3,894,938. A process employing a reactor with alternating dewaxing-hydrotreating beds is disclosed in U.S. Pat. No. 4,597,854. Reference is made to these patents for details of such processes.

Description of Catalysts

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. Medium pore aluminosilicate zeolites are favored for shape selective acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The catalysts which have been proposed for shape selective catalytic dewaxing processes have usually been zeolites which have a pore size which admits the straight chain, waxy n-paraffins either alone or with only slightly branched chain paraffins but which exclude more highly branched materials and cycloaliphatics. Intermediate pore size zeolites such as ZSM-5 and the synthetic ferrierites have been proposed for this purpose in dewaxing processes, as described in U.S. Pat. Nos. 3,700,585 (Re 28,398); 3,894,938; 3,933,974; 4,176,050; 4,181,598; 4,222,855; 4,259,170; 4,229,282; 4,251,499; 4,343,692, and 4,247,388. The hydrodewaxing catalysts preferred for use herein include the medium pore (i.e., about 5–7 A) shape selective crystalline aluminosilicate zeolites having a silica-to-alumina ratio of at least 12, a constraint index of about 1 to 12 and significant Bronsted acid activity. The fresh or reactivated catalyst preferably has an acid activity (alpha value) of about 45 to 400. Representative of the intermediate pore size zeolites are ZSM-5 (U.S Pat. No. 3,702,886), ZSM-11 (U.S. Pat. No. 3,709,979), ZSM-22, ZSM-23 (U.S. Pat. No. 4,076,842), ZSM-35 (U.S. Pat. No. 4,016,245), ZSM-48 (U.S. Pat. No. 4,375,573), ZSM-57, and MCM-22 (U.S. Pat. No. 4,954,325). The disclosure of these patents are incorporated herein by reference. While suitable zeolites having a coordinated metal oxide to silica molar ratio of 20:1 to 200:1 or higher may be used, it is advantageous to employ a standard aluminosilicate ZSM-5 having a silica:alumina molar ratio of about 25:1 to 70:1, suitably modified to obtain an acid cracking activity (alpha value) less than 300. A typical zeolite catalyst component having Bronsted acid sites may consist essentially of crystalline aluminosilicate having the structure of ZSM-5 zeolite with 5 to 95 wt. % silica, clay and/or alumina binder. It is understood that other medium pore acidic metallosilicates, such as silica-aluminophosphates (SAPO) materials may be employed as catalysts.

These siliceous materials may be employed in their acid forms, substantially free of hydrogenation-dehydrogenation components, or with these components added such as the noble metals of Group VIIIA, especially platinum, palladium, rhenium or rhodium, also, e.g., nickel, cobalt, molybdenum, tungsten, copper or zinc.

Intermediate pore size pentasil zeolites are particularly useful in the process because of their regenerability, long life and stability under the extreme conditions of operation. Usually the zeolite crystals have a crystal size from about 0.01 to over 2 microns or more, with 0.02–1 micron being preferred. Fixed bed catalyst may consist of a standard 70:1 aluminosilicate H-ZSM-5 extrudate having an acid value less than 1400, preferably about 100–300.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 in U.S Pat. No. 3,354,078, in the Journal of Catalysis, Vol. 4, p. 527 (1965); Vol. 6, p. 278 (1966); and Vol. 61, p. 395 (1980), each incorporated herein by reference as to that description. The experimental conditions of the text used herein include a constant temperature of 538° C. and a variable flow rate as described in detain in the *Journal of Catalysis,* Vol. 61, p. 394.

Catalyst size can vary widely within the inventive concept, depending upon process conditions and reactor structure. If a low space velocity or long residence in the catalytic reaction zone is permissible, catalysts having an average maximum dimension of 1 to 5 mm may be employed.

A reactor configuration as described in U.S. Pat. No. 5,246,568 may be employed.

Hydrotreating

The employment of a hydrotreating step following the dewaxing offers further opportunity to improve product quality without significantly affecting its pour point. The metal function on the hydrotreating catalyst is effective in varying the degree of desulfurization in the same way as the metal function on the dewaxing catalyst. Thus, a hydrotreating catalyst with a strong desulfurization/hydrogenation function such as nickel-molybdenum or cobalt-molybdenum will remove more of the sulfur than a weaker desulfurization function such as molybdenum. Thus, because the retention of certain desired sulfur compounds is related to superior oxidative stability, the preferred hydrotreating catalysts will comprise a relatively weak hydrodesulfurization function on a porous support. Because the desired hydrogenation reactions require no acidic functionality and because no conversion to lower boiling products is desired in this step, the support of the hydrotreating catalyst is essentially non-acidic in character. Typical support materials include amorphous or crystalline oxide materials such as alumina, silica, and silica-alumina of non-acidic character. The metal content of the catalyst is typically up to about 20 weight percent for base metals with lower proportions being appropriate for the more active noble metals such as palladium. Hydrotreating catalysts of this type are readily available from catalyst suppliers. These catalysts are generally presulfided using $H_2S$ or other suitable sulfur containing compounds. The degree of desulfurization activity of the catalyst may be found by experimental means, using a feed of known composition under fixed hydrotreating conditions. Control of the reaction parameters of the hydrotreating step also offers a useful way of varying the product properties. As hydrotreating temperature increases the degree of desulfurization increases; although hydrogenation is an exothermic reaction favored by lower temperatures, desulfurization usually requires some ring-opening of heterocyclic compounds to occur and these reactions, are favored by higher temperatures. If, therefore, the temperature during the hydrotreating step can be maintained at a value below the threshold at which excessive desulfurization takes place, products of improved oxidation stability are obtained. Using a metal such as molybdenum on hydrotreating catalyst temperatures of about 400°–700° F. (about 205°–370° C.), preferably about 500°–650° F. (about 260°–345° C.) are recommended for good oxidative stability. Space velocity in the hydrotreater also offers a potential for desulfurization control with the higher velocities corresponding to lower severities being appropriate for reducing the degree of desulfurization. The hydrotreated product preferably has an organic sulfur content of at least 0.10 wt. percent or higher e.g. at least 0.20 wt. percent, e.g. 0.15–0.20 wt. percent.

Variation of the hydrogen pressure during the hydrotreating step also enables the desulfurization to be controlled with lower pressures generally leading to less desulfurization as well as a lower tendency to saturate aromatics, and eliminate peroxide compounds and nitrogen, all of which are desirable. A balance may therefore need to be achieved between a reduced degree of desulfurization and a loss in the other desirable effects of the hydrotreating. Generally, pressures of 200 to 1000 psig (about 1480 to 7000 kPa abs) are satisfactory with pressures of 400 to 800 psig (about 2860 to 5620 kPa abs) giving good results with appropriate selection of metal function and other reaction conditions made empirically by determination of the desulfurization taking place with a given feed.

Products

The products are lubricating oil stocks of good pour point, viscosity, viscosity index, cloud point and overnight clouding characteristics.

Pour point is the lowest temperature at which a petroleum oil will flow or pour when it is chilled without disturbance at a controlled rate. Pour point is an important specification for products used in cold climates. Pour point is measured according to ASTM-D-97 as published by ASTM, 1916 Race Street, Philadelphia Pa.

Viscosity is the property of liquids under flow conditions which causes them to resist instantaneous change of shape or rearrangement of their parts due to internal friction. Viscosity is generally measured as the number of seconds, at a definite temperature, required for a standard quantity of oil to flow through a standard apparatus. Measurements include Saybolt Universal Viscosity (SUS) and Kinematic (centiStokes).

Viscosity index (V.I.) is a quality parameter of considerable importance for distillate lubricating oils to be useful in automotive and aircraft engines subject to wide variations in temperature. This index is a series of numbers from 0 to 100 or higher and indicates the degree of change of viscosity with temperature. The higher the V.I., the smaller its change in viscosity for a given change in temperature. A high V.I. of 100 delineates an oil that does not tend to become viscous at low temperatures or become thin at high temperatures. Measurement of the Saybolt Universal Viscosity of an oil at 100° F. (38° C.) and 210° F. (99° C.) and referral to correlations, provides a measure of the V.I. of the oil. V.I. is as noted in the Viscosity Index Tabulations of the ASTM (D567) published by ASTM, 1916 Race Street, Philadelphia, Pa. or equivalent.

Cloud Point is the temperature at which solidifiable compounds present in the sample begin to crystallize or separate from the solution under a method of prescribed chilling and is measured by ASTM-D-2500.

The dewaxing mechanism of catalytic hydrodewaxing is different than that of solvent dewaxing, resulting in some differences in product chemical composition. Catalytically dewaxed products produce a haze on standing at 10° F. (−12° C.) above specification pour point for more than twelve hours, known as the Overnight Cloud (ONC) formation. The extent of this ONC formation is less severe with solvent dewaxing.

The following non-limiting examples illustrate the invention.

Comparative Example 1

High Density Alumina-Bound HZSM-5 Extrudate

A physical mixture of 20 parts alumina (Pural SB III, Condea) and 80 parts ZSM-5 with a small crystal size (0.02–0.05 microns) were mulled to form a uniform mixture. The mixture was auger extruded to 1/16" cylindrical shapes and dried at 250° F. The dried catalyst was then ammonium exchanged to remove sodium ions and then washed with deionized water. The catalyst was then calcined in nitrogen for 3 hours at 900° F. and finally in air at 1000° F. for 6 hours. The catalyst was finished by steaming in 100% steam for 5 hours at 900° F.

Comparative Example 2

Low-Density Alumina Bound HZSM-5 Extrudate

A physical mixture of 35 parts alumina (Versal, LaRoche) and 65 parts ZSM-5 were mulled with water to form a uniform mixture. The mixture was extruded, calcined and steamed as in Example 1.

Comparative Example 3

Preparation of Inorganic Silica Bound HZSM-5 Extrudate

A physical mixture of 10 parts silica powder (Nasilco Ultrasil VN3SP), 10 parts colloidal silica (Du Pont HS-30 Ludox) and 80 parts ZSM-5 of small crystal size were mulled, extruded, ammonium exchanged and calcined as in Example 1. The catalyst was finished by steaming in 100% steam for 12 hours at 750° F. for higher activity than the extrudate of Example 1.

Comparative Example 4

Preparation of Inorganic Silica Bound HZSM-35 Extrudate

A physical mixture of 10 parts silica powder (Nasilco Ultrasil VN3SP), 10 parts colloidal silica (Du Pont HS-30 Ludox) and 80 parts ZSM-35 of small crystal size were mulled, extruded, ammonium exchanged, and calcined as in Example 1. This catalyst was used unsteamed. Steaming of this catalyst would reduce activity and level of pour point conversion in dewaxing to unacceptable levels. ZSM-35 is an intermediate pore zeolite which is in the ferrierite family. These zeolites are more constrained than ZSM-5 and therefore should be more selective for the smaller molecules which result from dewaxing. ZSM-35 has a 15° F. low pour point limit with Isthmus 170N raffinate.

Example 5

Preparation of Organic Silica Bound HZSM-5 Extrudate

A physical mixture of 12 parts by weight silicone resin (Dow Corning Q6-2230), 56 parts by weight small crystal size ZSM-5, 4 parts by weight cellulose methylether (Methocel), 12 parts iso-propanol and 16 parts water were mulled, extruded, calcined and steamed as in Example 1. The calcined extrudate contained 90 parts zeolite and 10 parts silica.

The composition contained a majority of its pore volume (e.g. over 60%) in the size range of 300 Angstroms or above.

Example 6

The catalysts prepared in Example 1, 3, 4 and 5 were used in a dewaxing process.

For each catalyst, 15 or 20 cc volumes of catalyst were packed into small-scale downflow reactors using sand to fill interstitial volume to inhibit by-passing. Furfural-extracted Isthmus and Arab light raffinates were used as feedstock. The lubricant raffinates were dewaxed to various pour points in the range of 0° F. to 40° F. Dewaxing Conditions included one LHSV, 400 psig, about 2500 scf/bbl $H_2$ and a temperature to achieve desired optimum pour point.

Lube basestock yields and viscosity indices (V.I.) at 20° F. pour point attained over each catalyst for the various feedstocks are shown in Table 1.

TABLE 1

| | Raffinates | | | | |
|---|---|---|---|---|---|
| Catalysts | Isthmus 100N | Isthmus 170N | Arab Lt 160T | Arab Lt 700N | Arab Lt 150 BS |
| HZSM-5/alumina (Ex. 1) | | | | | |
| % Lube Yield | 80.0 | 79.9 | 80.5 | | |
| VI | 96 | 99 | 105 | 90 | 95 |
| HZSM-5/Organic SiO$_2$ (Ex. 5) | | | | | |
| % Lube Yield | 79.7 | 82.6 | 80.7 | 87.1 | 91.0 |
| VI | 98 | 101 | 106 | 90 | 95 |
| HZSM-5/Inorganic SiO$_2$ (Ex. 3) | | | | | |
| % Lube Yield | — | — | 79.3 | 85.1 | 87.0 |
| VI | — | — | 103 | 88 | 95 |
| HZSM-35/Inorganic SiO$_2$ (Ex. 4) | | | | | |
| % Lube Yield | — | 85.3 | 83.0 | — | — |
| VI | — | 102 | 108 | — | — |

VI = viscosity index

The alumina-bound catalyst of Example 1 is considered the basic comparative catalyst because it is representative of the best commercial catalyst presently available. A linear relationship for yield and V.I. was found for each of the catalysts in processing the various raffinate feedstocks.

Overall the results using the catalyst prepared according to the invention (Example 5) attained the best results. The improvement was most pronounced with the automotive-grade Isthmus neutral (170N) raffinate. Also improvements using this catalyst were shown in basestock V.I. with Arab light neutral (turbine-grade) 160N raffinate, and a very light feedstock, Isthmus (automotive-grade) 100N raffinate.

In comparison with inorganic silica bound catalysts of Ex. 3, with catalysts prepared according to the invention yield and V.I. improvements were seen for light neutral as well as heavy neutral raffinates.

In comparison with inorganic silica bound HZSM-35 of Ex. 4 with more restricted pores, a similar basestock V.I. is obtained with the invention in processing the automotive grade Isthmus 170N raffinate, but not with the Arab light turbine grade 160 T raffinate. More than compensating for this is the fact that the catalysts of the invention have no pour point limitations like HZSM-35 catalysts (15° F. low pour limit with Isthmus 170N raffinate) and is able to process heavy stocks (heavy neutral and bright stock raffinates).

It is concluded that catalytic dewaxing of lubricant raffinates with an HZSM-5 bound and extruded with silica wherein the source of silica is an organic silicone or silicone emulsion gives improved basestock yields and viscosity indices relative to identical dewaxing over alumina bound HZSM-5 or inorganic silica bound HZSM-5.

Example 7

The catalysts prepared in Example 1, 2, 3 and 5 were used to dewax bright stock.

For each catalyst, 15 or 20 cc volumes of catalyst were packed into small-scale downflow reactors using sand to fill interstitial volume to inhibit by-passing. Feedstocks designated D97, D2500, M1345 and M1345-9 were dewaxed over the catalysts. These furfural-extracted Arab Light bright stock furfural raffinates were dewaxed with the various catalysts to pour point in the useful range of 0° F. to 30° F. at 1 LHSV.

The resulting lubricant basestocks were subjected to an Overnight Cloud Tests (ONC) performed at 30° F. (M1345) and 46° F. (M1345-9) measured after at least 18 hours in a relative turbidity unit. The results are shown in Table 2.

TABLE 2

Catalyst Preparation Effects on Arab Light Bright Stock Pour Point, Cloud Point and Overnight Clouding Performance

| Catalyst Ex. # | D97 P. Pt. (°F.) | D2500 Cloud Pt. (°F.) | M1345 ONC @ 30° F. | M1345-9 ONC @ 46° F. |
|---|---|---|---|---|
| 2 | 0 | 0 | 20 | <1 |
| " | 5 | 28 | 98 | 15 |
| " | 15 | 26 | 45 | 7 |
| " | 15 | 20 | 64 | 9 |
| 1 | 20 | 56 | 385 | 209 |
| " | 20 | 32 | 143 | 54 |
| " | 20 | 28 | 98 | 21 |
| " | 25 | 32 | 164 | 71 |
| " | 25 | 32 | 155 | 72 |
| " | 30 | 30 | 115 | 38 |
| " | 30 | 54 | 212 | 79 |
| " | 30 | 38 | 153 | 26 |
| 3 | 15 | 36 | 83 | 21 |
| " | 25 | 48 | 129 | 55 |
| 5 | 0 | 14 | 30 | 10 |
| " | 5 | 42 | 181 | 24 |
| " | 10 | 24 | 59 | 3 |
| " | 10 | 24 | 63 | 4 |
| " | 10 | 14 | 82 | 5 |
| " | 10 | 32 | 126 | 8 |
| " | 25 | 36 | 116 | 5 |

TABLE 2-continued

Catalyst Preparation Effects on Arab Light Bright Stock Pour Point, Cloud Point and Overnight Clouding Performance

| Catalyst Ex. # | D97 P. Pt. (°F.) | D2500 Cloud Pt. (°F.) | M1345 ONC @ 30° F. | M1345-9 ONC @ 46° F. |
|---|---|---|---|---|
| " | 25 | 38 | 104 | 6 |
| " | 25 | 38 | 138 | 13 |
| " | 25 | 38 | 141 | 10 |
| " | 25 | 36 | 133 | 7 |
| " | 25 | 36 | 142 | 11 |
| " | 30 | 40 | 141 | 15 |
| " | 30 | 38 | 129 | 7 |

ONC measured after 18 hours + in relative turbidity unit from 0 (= clear) to 1000 (= opaque)

The high-density alumina bound comparative catalyst of Example 2 is representative of the best commercial lube raffinate dewaxing catalyst presently available. The results showed a pronounced and unexpected improvement in lube basestock hazing characteristics in dewaxing over catalysts prepared according to the invention (Example 5). In comparison with inorganic silica bound catalysts based on extrusion with inorganic silicon sources, this improvement using the catalyst of the invention was also observed.

Using the invention allows reduced dewaxing severity to meet cloud point/hazing specification. This confers lube yield benefits and longer cycle lengths.

We claim:

1. A process for catalytically dewaxing a hydrocarbon feedstock comprising contacting the feedstock with a catalyst composition which comprises a zeolite in an inert binder, the catalyst composition having been prepared by a method comprising mulling zeolite crystals, organosilicon compound, organic polymer and an extrusion facilitating amount of liquid to form an extrusion mixture, extruding the mixture to form an extrudate and calcining the extrudate to provide the catalyst composition.

2. The process of claim 1 wherein the zeolite has a Constraint Index of about 1 to about 12.

3. The process of claim 1 wherein the hydrocarbon feedstock comprises a lubricant raffinate.

4. The process of claim 3 wherein the lubricant raffinate is selected from the group consisting of light neutral, heavy neutral, and bright stock raffinates and mixtures thereof.

5. The process of claim 1 wherein the organosilicon compound is a silicone.

6. The process of claim 1 wherein the zeolite comprises from about 50 to about 95 wt. percent of the catalyst composition.

* * * * *